United States Patent [19]

Vanlerberghe et al.

[11] Patent Number: 4,971,789
[45] Date of Patent: Nov. 20, 1990

[54] IONIC POLYETHERS, PROCESS FOR PREPARING THEM AND COMPOSITIONS IN WHICH THEY ARE PRESENT

[75] Inventors: Guy Vanlerberghe, Claye-Souilly; Henri Sebag, Paris, both of France

[73] Assignee: L'Oreal, Paris, France

[21] Appl. No.: 678,405

[22] Filed: Dec. 5, 1984

[30] Foreign Application Priority Data

Dec. 7, 1983 [LU] Luxembourg ............................. 85122

[51] Int. Cl.$^5$ ............................................. A61K 7/06
[52] U.S. Cl. ......................................................... 424/70
[58] Field of Search .............................. 562/581, 426;
260/501.15; 564/292; 252/193; 8/405, 426;
514/179; 424/70

[56] References Cited

FOREIGN PATENT DOCUMENTS 2080303 2/1982 United Kingdom ................. 562/426

*Primary Examiner*—Bruce Gray
*Attorney, Agent, or Firm*—Cushman, Darby & Cushman

[57] ABSTRACT

Mixture of ionic polyethers of formula:

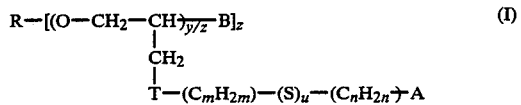

where
R denotes $C_1$-$C_{20}$ alkyl or alkenyl or $C_6$-$C_{20}$ aryl or aralkyl;
z=1 or 2; y=3-20; T=0 or S; u=0 or 1; m=3-11; n=0-11;
n≠0 when u=1 and m+n≧4; B=OH or A; A is an ionic group —COOM; —($CH_2$)$_u$—S—(W)COOH (with W=—$CH_2$—, —$CH_2$—$CH_2$— or —CH($CH_3$)— and u'=u); —$CH_2$—O—S)$_3$M, (M being an alkali metal or an ammonium ion optionally substituted by methyl, ethyl, hydroxyethyl, hydroxypropyol, methylhydroxypropyl or methyldihydroxypropyl);

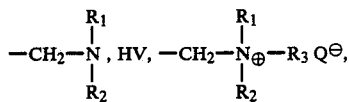

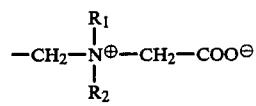

(where $R_1$, $R_2$ and $R_3$ denotes methyl, ethyl, hydroxyethyl or dihydroxypropyl, $R_1$ and $R_2$ being capable of forming with N an amino or ammonio heterocyclic ring, HV is an inorganic or organic acid and Q- is an anion);

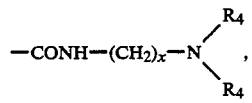

HV (with $R_4$=methyl or ethyl and x=2 or 3)

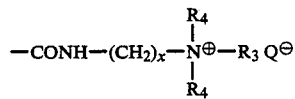

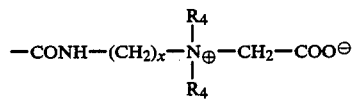

with the provision that when T=0 and u=0, A denotes only (b);

and process for preparing them.

The new polyethers can be employed in cosmetics, pharmacy and the textile industry as a result of their good solubilising and stabilising capacity.

25 Claims, No Drawings

IONIC POLYETHERS, PROCESS FOR PREPARING THEM AND COMPOSITIONS IN WHICH THEY ARE PRESENT

The present invention relates to new ionic polyethers, process for preparing them and their use in aqueous or aqueous-alcoholic compositions, particularly for cosmetic, pharmaceutical or textile use.

The new ionic polyethers according to the invention are in fact mixtures of compounds having a comb-shaped structure, consisting mainly of a polyether chain and long, regularly distributed branches ending in ionic groups.

Ionic surfactants are known for their generally good solubilizing properties above their critical micelle concentration, but they are frequently poorly tolerated from a biological standpoint.

On the other hand, the new compounds according to the invention possess, in addition to a good solubilizing capacity towards active compounds such as colorants or pharmaceutical compounds, a good stabilizing capacity towards some of these active compounds which are sensitive to oxidation, for example, and a low toxicity by a cutaneous route or towards the mucosa of the eye.

The ionic polyethers according to the present invention are therefore of great interest from a practical standpoint.

The compounds of the invention may be represented by the following general formula (I):

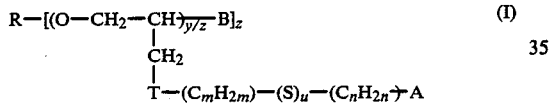

in which:
R denotes an alkyl or alkenyl radical containing 1 to 20 carbon atoms, or an aryl or alkylaryl radical containing 6 to 20 carbon atoms, which are interrupted if appropriate by one or more oxygen atoms, the said radical having the valency z, z being capable of being equal to 1 or 2;
y denotes an integer or decimal from 3 to 20;
T denotes an oxygen atom or a sulphur atom;
u denotes 0 or 1; when u=0, n=0; when u=1, n≠0 and R may be substituted by a radical S—$(C_nH_{2n})$—A;
m denotes an integer from 3 to 11;
n denotes either 0, or an integer from 1 to 11, the sum m+n>0 and preferably m+n≧10.
B denotes the OH group or the group A;
A being an ionic group chosen from the various following groups:
(a) —COOM
(b) —$(CH_2)_{u'}$—S—(W)COOM, W denoting —$CH_2$—; —$CH_2$—$CH_2$—; or

u' being equal to 0 or 1 and u'=u
(c) —$CH_2$—O—$SO_3M$
in which M denotes an alkali metal, preferably lithium, sodium or potassium, or an ammonium ion optionally substituted by one or more methyl, ethyl, hydroxyethyl, hydroxypropyl, methylhydroxypropyl, or methyldihydroxypropyl groups;

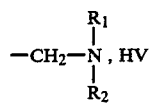

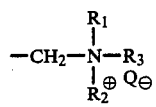

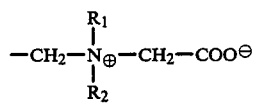

where
$R_1$, $R_2$, $R_3$, which are identical or different, denote methyl, ethyl, hydroxyethyl or dihydroxypropyl radicals, $R_1$ and $R_2$ being also capable of forming with the nitrogen atom a heterocyclic amino and ammonio group; HV denotes an inorganic or organic acid, and preferably hydrochloric acid, lactic acid, acetic acid, methanesulphonic acid or p-toluenesulphonic acid;
$Q^\ominus$ denoting an anion, and preferably $Br^\ominus$, $Cl^\ominus$, $I^\ominus$, $CH_3SO_4^\ominus$, $CH_3SO_3^\ominus$ or

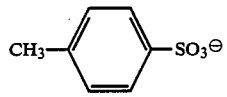

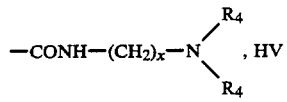

$R_4$ denoting methyl or ethyl
X=2 or 3 and HV having the same meaning as above

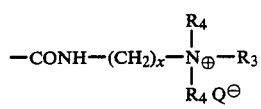

$R_3$ and Q having the same meaning as above

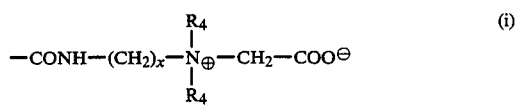

with the provision that when T=0 and u=0, A denotes only the group (b).

In the compounds of formula (I) above, when the group A has the meanings (g), (h) or (i), B denotes the OH group; when the group A has the meanings (b), (c), (d), (e) or (f), the group B has the same meaning as A; when the group A has the meaning (a), the group B can have either the meaning OH, or the same meaning as A.

The preferred compounds according to the invention are those in which m+n≧10 and y denotes an integer or decimal from 5 to 20.

When u=n=0 and A=COOM, the preferred compounds are those for which m≧10.

The compounds according to the invention of formula (I) are obtained according to three- or four-stage procedures, each of these stages corresponding to reactions of conventional organic chemistry.

The compounds of formula (I) in which T=S are prepared according to a process comprising:

a first stage in which a polyaddition is carried out of an epihalohydrin, and preferably epichlorohydrin, to a compound having alcohol or phenol group(s), of valency z and of formula (IV) according to the following reaction scheme:

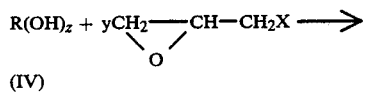

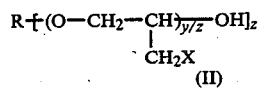

to obtain a mixture of halogenated oligoethers of formula (II) in which R, y and z have the same meanings as above and X denotes bromine or preferably chlorine, y corresponding to the molar ration epoxide/compound (IV), each of the oligomers in the mixture being capable of containing in reality a number of units which is smaller than, equal to, or greater than y;

a second stage in which the mixture of halogenated oligoethers of formula (II) is reacted with α, ω-mercaptoacids, their methyl or ethyl esters, or with mercaptoalkanols to obtain the mixtures of intermediate compounds (V) according to the following reaction scheme:

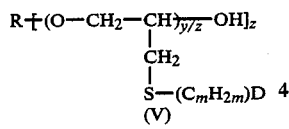

where R, m, y and z have the same meanings as above and D denotes one of the groups

| | |
|---|---|
| COOH | (E) |
| COOCH₃ or COOC₂H₅ | (F) |
| CH₂OH | (G); | a third stage in which the intermediate compounds of formula (V) are modified chemically to obtain the compounds of formula (I) according to the invention.

The compounds of formula (I) according to the invention in which T=0 are prepared according to a process comprising:

a first stage in which a polyaddition is carried out of an alkenyl glycidyl ether such as, for example, allyl glycidyl ether or undecenyl glycidyl ether, to a compound containing alcohol or phenol group(s), of valency z and of formula (IV), according to the following reaction scheme:

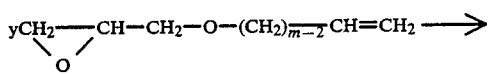

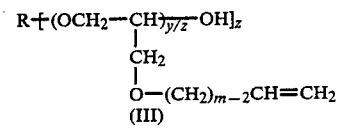

to obtain a mixture of unsaturated oligoethers of formula (III) in which R, m, y and z have the same meanings as above, y corresponding to the molar ratio epoxide/compound (IV), each of the oligomers in the mixture being capable of containing in reality a number of units which is smaller than, equal to, or greater than y;

a second stage in which the mixture of oligomers of formula (III) is reacted with α,ω-mercaptoacids, their methyl or ethyl esters or with mercaptoalkanols to obtain a mixture of intermediate compounds of formula (VI) according to the following reaction scheme:

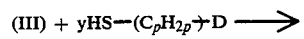

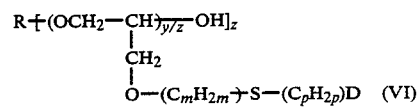

R, m, y and z having the same meanings as above,
p denoting an integer from 1 to 10 and
D denoting one of the groups

| | |
|---|---|
| COOH | (E) |
| COOCH₃ or COOC₂H₅ | (F) |
| CH₂OH | (G); | a third stage in which the intermediate compounds of formula (VI) are chemically modified to obtain the products (I) according to the invention.

When the starting compounds (IV) are unsaturated, the group R of the compounds (I) for which u=1, which are derived from the compounds (VI), may contain as a substituent the group S—(C$_n$H$_{2n}$)—A.

The reactants of formula (IV) which can be employed in the process of the invention contain from 1 to 20 carbon atoms and are chosen, for example, from:
saturated or unsaturated monoalcohols,
ethers of ethylene glycol or of poly(ethylene glycol)
glycerol monoethers
1,2-, 1,3- or α,ω-alkanediols
phenol
alkylphenols such as octyl- or nonylphenol
glycol phenyl or alkylphenyl ethers
diphenols such as bisphenol A.

The first stage of the process for preparing the compounds of formula (I) in which T=S or 0 is carried out by progressive addition of the epihalohydrin or of the alkenyl glycidyl ether to the compound of formula (IV), at a temperature of between 30° and 100° C., preferably 50° to 80° C., in the presence of a catalyst such as BF₃ in the form of an acetic or ether complex, or of SnCl₄.

In general the reaction takes place in the absence of solvent, but hydrocarbon or hydrochlorocarbon solvents such as, for example, hexane, heptane, benzene, toluene, methylene chloride, or dichloroethane are sometimes employed.

The second stage of the process for preparing the compounds of formula (I) in which T=S is carried out by heating α,ω-mercaptocarboxylic acids, their methyl or ethyl esters or mercaptoalkanols at a temperature of between 60° and 110° C., in the presence of solvents such as $C_1$–$C_4$ alcohols, ethers of these alcohols with ethylene glycol and, if appropriate, in the presence of water, with the oligomers (II) in the presence of sodium or potassium methoxide or ethoxide, sodium hydroxide or potassium hydroxide.

The second stage of the process for preparing the compounds of formula (I) in which T=0 is carried out by heating the α,ω-mercaptocarboxylic acids, their methyl or ethyl esters or mercaptoalkanols at a temperature of between 60° and 110° C., in the presence of solvents such as $C_1$–$C_4$ alcohols, ethers of these alcohols with ethylene glycol and, if appropriate, in the presence of water, with the oligomers of formula (III) in the presence of free radical initiators such as azobisisobutyronitrile or benzoyl peroxide, or in the presence of strong acids such as sulphuric acid, phosphoric acid, hydrochloric acid or p-toluenesulphonic acid.

The chemical reactions which constitute the third stage of the process for preparing the compounds of formula (I) are reactions which are well known to the specialist; some of them are nevertheless described in detail in the examples of preparation which follow.

To prepare the compounds according to the invention of formula (Ia), a neutralization is carried out of the compounds of formulae $(V)_{(E)}$ or $(VI)_{(E)}$ or a saponification of the compounds of formulae $(V)_{(F)}$ or $(VI)_{(F)}$.

"A compound of formula (Ia)" denotes a compound of formula (I), a formula in which A denotes the group (a).

"A compound of formula $(V)_{(E)}$ or $(VI)_{(F)}$" denotes a compound of formula (V) in which D denotes the group E or a compound of formula (VI) in which D denotes the group F.

These explanations also apply to the other compounds denoted in a similar manner.

It is also possible to carry out an esterification of the compounds $(V)_{(G)}$ with methanesulphonyl chloride or p-toluenesulphonyl chloride, followed by a reaction with mercaptocarboxylic acids or their derivatives and, if appropriate, a neutralization leading to the compounds of formula (Ia).

The compounds of formula $I_{(g)}$ are prepared by reacting compounds $V_{(F)}$ or $VI_{(F)}$ with a primary-tertiary amine of formula:

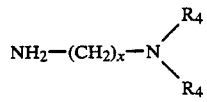

followed by neutralization. Alkylation of the compounds $I_{(g)}$ with a compound of formula $R_3Q$ gives the compounds of formula $I_{(h)}$; reaction of chloroacetic acid or of its salts with the compounds $I_{(g)}$ gives the compounds of formula $I_{(i)}$.

The compounds of formula $I_{(c)}$ are obtained by sulphating the compounds $V_{(G)}$ or $VI_{(G)}$ with sulphuric chlorohydrin and neutralizing.

The compounds $I_{(b)}$ are obtained by esterifying the compounds $V_{(g)}$ or $VI_{(G)}$ with methanesulphonyl chloride or p-toluenesulphonyl chloride followed by reaction with the mercaptocarboxylic acids or their derivatives.

The compounds of formula $I_{(d)}$ are obtained by esterifying the compounds $V_{(G)}$, $VI_{(G)}$ with methane-sulphonyl chloride or p-toluenesulphonyl chloride, followed by reaction with secondary amines of formula:

The compounds of formula $I_{(e)}$ are derived from the compounds $I_{(d)}$ by quaternization of the latter with an alkylating agent $R_3Q$.

These compounds of formula $I_{(e)}$ can also be obtained by esterifying the compounds $V_{(G)}$ or $VI_{(G)}$ with methanesulphonyl chloride or p-toluenesulphonyl chloride, followed by reaction with tertiary amines of formula:

Q in the formula $I_{(e)}$ denoting, in this case:

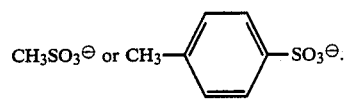

The compounds of formula $I_{(f)}$ are derived from the compounds $I_{(d)}$ by reaction with chloroacetic acid or with its salts.

Among the secondary amines which may be employed for the preparation of the compounds $I_{(d)}$ and the compounds $I_{(e)}$ and $I_{(f)}$ derived from $I_{(d)}$, may be mentioned, as examples, dimethylamine, diethylamine, piperidine, morpholine, N-methyl-N-hydroxyethylamine or N-ethyl-N-hydroxyethylamine.

Among the tertiary amines of formula:

which may be employed for the preparation of the compounds $I_{(e)}$ may be mentioned dimethylhydroxyethylamine, trimethylamine, methylpiperidine or methylmorpholine.

The compounds according to the invention are, throughout their method of preparation, families of homologues of various degrees of polymerization distributed around an average value corresponding to the number of epoxide molecules employed per molecule of compound (IV).

Occasionally, for some applications, use is made of combinations of two families of compounds (I) incorporating, in particular, groups A which may be different. These combinations of compounds of formula (I) are also the subject of the present invention and are also denoted by the compounds of formula (I) or compounds according to the invention.

The compounds of formula (I) according to the invention are generally water-soluble and are preferably employed in aqueous solution; nevertheless, for some applications, for example in dyeing, the addition of solvents such as $C_2$-$C_4$ alcohols or Cellosolves may be advantageous to improve the appearance of the formulation or the coloring treatment.

The compounds according to the invention may be employed at weight concentrations of 0.1 to 35% and preferably from 0.2 to 10%.

A subject of the present invention is therefore also an aqueous or aqueous-alcoholic composition containing 0.1 to 35% and preferably 0.2 to 10% by weight of compounds of formula (I).

The aqueous composition defined above, optionally containing solvents, may also contain surface-active agents or polymers of an anionic, cationic, amphoteric, zwitterionic or nonionic character, proteins, colorants, pharmaceutically active principals, sunscreens, perfumes, preserving agents, thickeners, opacifiers or electrolytes.

It is advantageous to combine a compound or a mixture of compounds of formula (I) where A denotes an anionic group with a compound or a mixture of compounds where A denotes a cationic group. It is also possible to combine a compound of formula (I) where A denotes an anionic group with a cationic polymer or to combine a compound of formula (I) where A denotes a cationic group with an anionic polymer.

In general, the compounds according to the invention have good solubilizing properties for active compounds such as hair dyes or compounds for pharmaceutical use such as, for example, hydrocortisone. Sometimes they offer the advantage of retarding the decomposition of unstable substances and are generally well tolerated from a physiological standpoint.

A cosmetic composition containing, in an aqueous or aqueous-alcoholic medium, an effective quantity of at least one dye or dye precursor and a compound or mixture of compounds of formula (I) in the weight concentration indicated above is therefore also a subject of the present invention.

A pharmaceutical composition containing an effective quantity of an active principal such as hydrocortisone combined in an aqueous or aqueous-alcoholic medium with the compounds of formula (I) in the weight concentration indicated above is also a subject of the present invention.

Finally, the present invention is also aimed at a composition for textile processing incorporating, in an aqueous or aqueous-alcoholic medium, an effective quantity of a dye and a compound or mixture of compounds of formula (I) in the concentration indicated above.

The cosmetic, textile or pharmaceutical compositions containing the compounds according to the invention may be in the form of solutions, emulsions, gels, creams or aerosols.

The present invention will be illustrated better with the aid of the following non-restrictive examples:

EXAMPLE I

Preparation of the mixture of compounds of formula (I) in which:

R denotes Na—OCO—$CH_2$—S—$C_{11}H_{22}$—
A denotes —COO—Na
B denotes —OH
T denotes —O—
m=11 n=1 u=1 y=5 z=1

(1) Preparation of the mixture of intermediate compounds (III)

0.25 ml of $BF_3$ etherate is added to 10.5 g (0.062 mole) of undecenyl alcohol followed, dropwise at 50° C. over 1 h 15, by 70 g (0.31 mole) of undecenyl glycidyl ether. The temperature is maintained for another 1 hour after the addition.

A viscous, colorless liquid, having an epoxide value of 0, is thus obtained.

(2) Preparation of the mixture of compounds of the invention 23.8 g (0.190 equivalent) of ethyl thioglycolate and 0.6 g of azobisisobutyronitrile are added to 40 g of the product obtained in this way (0.185 equivalent as ethylene group) and the reaction mixture is heated at 80° C. for 2 hours. The conversion is 95%.

18.5 g of sodium hydroxide at 10.3 meq/g strength, 40 ml of water and 30 ml of butanol are added, and the mixture is heated for 2 hours at 60° C.

The butanol and water are removed by distillation. A water-soluble white solid, with a COO$^\ominus$ value of 2.55 meq/g, is thus obtained.

EXAMPLE II

Preparation of the mixture of compounds of formula (I) in which:

R denotes Na—OCO—$CH_2$—S—$C_{11}H_{22}$—
A denotes —COO—Na
B denotes —OH
T denotes —O—
m=11, n=1 u=1, y=10, z=1

(1) Preparation of the mixture of intermediate compounds (III)

0.15 ml of $BF_3$ etherate, followed by 56.5 g (0.25 mole) of undecenyl glycidyl ether are added to 4.25 g (0.025 mole) of undecenyl alcohol as in example (I).

(2) Preparation of the mixture of compounds of the invention 0.9 g of azobisisobutyronitrile is added to 60 g of derivatives III obtained previously (0.275 equivalent as ethylene groups) followed by gradual addition of 33.5 g (0.275 mole) of ethyl thioglycolate while heating up to 50° C.

After a few moments, a heating causes the temperature to rise to 100° C. The mixture is cooled with a water bath and the temperature is then maintained at 80° C. for 1h 30. The conversion is then approximately 96%.

Saponification is carried out by adding 27.5 g of 40% strength sodium hydroxide in the presence of 30 g of water and of 40 g of butanol over 2 hours at 60° C. The mixture is acidified by adding 28.5 g of concentrated hydrochloric acid, separated and washed with water. It is dried under reduced pressure. A white wax is obtained (acid value=3 meq/g).

45 g of the acid compound obtained in this way are neutralized by adding 13.5 g of 40% strength sodium hydroxide and 13.5 g of water.

The final product is in the form of a white paste, soluble in water with a slight turbidity and having a COO$^\ominus$ value equal to 1.96 meq/g.

EXAMPLE III

Preparation of a mixture of compounds of formula (I) in which:
R denotes —$C_{12}H_{25}$
A denotes —COO—Na
B denotes —OH
T denotes —S—
m=11, n=0, u=0, y=10 and z=1

(1) Preparation of the mixture of intermediate compounds (II)

0.66 ml of $BF_3$ etherate is added to 37.2 g of 1-dodecanol (0.2 mole), followed, at 50° C. over 2h 30, by 185 g of epichlorohydrin (2 moles).

After one hour's stirring at 50° C. a very viscous brown product is obtained which has an epoxide value of 0.

(2) Preparation of the mixture of compounds of the invention 20 g of Methyl Cellosolve, 31 g (0.31 mole) of 40% strength sodium hydroxide and 20 g of water are added, under nitrogen, to 33.5 g (0.15 mole) of 11-thioundecanoic acid. The temperature is allowed to rise up to 75° C. and then 16.7 g (0.15 equivalent as chlorine) of the intermediate derivatives obtained earlier are added over 30 minutes.

The mixture is then heated to 100° C. for 2 hours.

The reaction mixture is diluted with 200 ml of water and acidified with 16.7 ml of concentrated hydrochloric acid. A solid is thus obtained which is filtered off and washed with water.

71 g of the solid obtained are taken up with 200 g of water and 190 g of 40% strength sodium hydroxide. A yellow-colored, slightly turbid solution containing 25% of active substance is obtained.

Preparation of the monoisopropanolamine salt where A where denotes COO$^\ominus$H$_3$N$^\oplus$—CH$_2$—CHOH—CH$_3$ 25 g of solution obtained in this way are acidified with 21 ml of normal hydrochloric acid.

The reprecipitated acid is washed with water and then neutralized with 1.43 g of monoisopropanolamine in the presence of 10 ml of water.

A viscous solution is obtained which, after cooling, forms a clear liquid gel containing 45% of A.S.

EXAMPLE IV

Preparation of a mixture of compounds of formula (I) in which:
R denotes —$C_{12}H_{25}$
A=B=

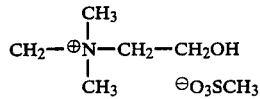

T denotes —S—
m=11, n=0, u=0, y=10, z=1

The mixture of intermediate compounds (II) is obtained as in example III.

42.5 g (0.2 mole) of 11-mercaptoundecanol are added to 22.2 g (0.2 equivalent as chlorine) of this mixture of intermediate compounds dissolved in 80 g of absolute ethanol, and then 36 g (0.21 mole) of sodium methoxide dissolved in methanol (5.84 meq.) are run in at 60° C. over 20 minutes. The mixture is then heated under reflux for 15 hours.

The sodium chloride is filtered off and the solvent is evaporated off under reduced pressure.

The mixture of compounds of general formula (V)$_{(G)}$ thus obtained is in the form of a white solid, the structure of which is confirmed by NMR.

55 g (0.217 equivalent) of this mixture are added to 22 g (0.217 mole) of triethylamine. 31.3 g (0.217 mole) of freshly distilled methanesulphonyl chloride are then added over 20 minutes and left stirred for 3 hours at 30° C.

The precipitate of triethylamine hydrochloride is filtered off and washed with dry toluene.

After evaporation of the solvent, 74 g of polymethanesulphonate, characterized by NMR, are obtained.

18 g (0.011 mole) of dimethylhydroxyethylamine are added under nitrogen to 72.5 g of product obtained in this way and heated for 3 hours at 60°–70° C. The reaction mixture gradually becomes thicker. It is taken up with 50 ml of acetone and heating is continued for a further 3 hours.

After evaporation of the solvent a water-soluble orange paste is obtained.

EXAMPLE V

Preparation of a mixture of compounds of formula (I) in which:
R denotes —$C_{12}H_{25}$
A denotes —COO—Na
B denotes —OH
T denotes —O—
m=3, n=10, u=1, y=10 and z=1.

(1) Preparation of the mixture of intermediate compounds of formula III 1 ml of $BF_3$ etherate is added to 55.8 g of 1-dodecanol (0.3 mole) followed, at 50° C. over 1 hour, by 342 g (3 moles) of allyl glycidyl ether.

After 30 minutes stirring it is found that the epoxide group has disappeared completely.

The mixture is in the form of a yellowish liquid, the structure of which is confirmed by NMR.

(2) Preparation of the mixture of compounds of formula (I)

0.5 g of azobisisobutyronitrile is added to 19.8 g of intermediate compounds obtained in this way and heated to 80° C., followed by dropwise addition over 30 minutes of 30.2 g (0.127 mole) of ethyl 11-mercaptoundecanoate. The reaction mixture is then heated for 4 hours.

After dilution with 50 ml of ethanol, 12.75 g of 40% strength sodium hydroxide, diluted previously with 50 ml of water, are added. The mixture is heated for 2 hours, the alcohol is distilled off and the product is then diluted to a concentration of 25% of active substance.

The solution obtained is yellow in color.

EXAMPLE VI

Preparation of a mixture of compounds (I) in which:
R denotes —$C_{12}H_{25}$
A denotes —COONa
B denotes —OH
T denotes —O—
m=3 n=1 u=1 y=10 z=1

33.1 g of intermediate compounds III prepared as described in example V (0.25 equivalent as ethylene group) are added dropwise at 75° C. to 25.6 g (0.21 mole) of ethyl thioglycolate dissolved previously in 50 ml of ethanol in the presence of 0.6 g of azobisisobutyronitrile. Addition time: 20 minutes. The mixture is then heated for 2 hours under reflux. 22 g of 40% strength sodium hydroxide diluted in 100 g of water are added next and then the mixture is heated for 1 hour at 70° C.

The ethanol is removed by evaporation and the residue taken up in water until an aqueous solution containing 44% of active substance, clear and yellow in color, is obtained. Base value: 1.95 meq/g.

EXAMPLE VII

Preparation of a mixture of compounds of formula (I) in which:
R denotes

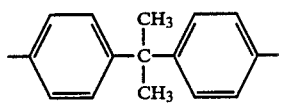

A denotes —COONa
B denotes —OH
T denotes —O
m=3 n=1 u=1 y=15 z=2

I—Preparation of the mixture of intermediate compounds of formula III:

1 ml of BF$_3$ etherate is added to 45.6 g (0.2 mole) of bisphenol A dispersed in 100 ml of dichloroethane, followed by dropwise addition at 55° C. of 342 g (3 moles) of allyl glycidyl ether. Addition time: 1 hour. The reaction is exothermic. After 1 hour the reaction is complete. The mixture is clear and dark yellow in color. The solvent is evaporated off under reduced pressure. 395 g of residual material are obtained, with an epoxy value of 0.

II—Preparation of the mixture of compounds of formula I:

27.5 g (0.225 mole) of ethyl thioglycolate are dissolved in 100 ml of ethanol. 0.56 g of azobisisobutyronitrile is added, followed, at 70° C., by 29 g of intermediate products III obtained earlier (0.225 equivalent) and dissolved previously in 50 ml of ethanol. Addition time: 30 minutes. Heating is then continued for 2 hours. The conversion is then 94% according to the mercaptane value. 22.5 g of 40% strength sodium hydroxide are added and the mixture is heated for 1 hour at 75° C. The alcohol is then distilled off with gradual addition of water until a yellow aqueous solution is obtained containing 35% of active substance, with a base value of 1.45 meq/g.

EXAMPLE VIII

Preparation of a mixture of compounds of formula (I) in which:
R denotes

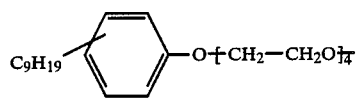

A denotes S—CH$_2$—CH$_2$—COOH
B denotes —OH
T denotes —O—
m=3 n=0 u=0 y=8 z=1

I—Preparation of the mixture of intermediate compounds III 0.5 ml of BF$_3$ etherate is added to 39.6 g (0.1 mole) of polyoxyethylated nonylphenol containing 4 ethylene oxide units (Remcopal 334), followed, at 50°–60° C., by 91.2 g (0.8 mole) of allyl glycidyl ether, added dropwise over 2 hours.

After further heating for 2 hours, a liquid product is obtained, yellow in color and with an epoxide value of 0.

II—Preparation of the mixture of compounds of formula (I)

100 ml of ethyl alcohol, 42.4 g (0.4 mole) of mercaptopropionic acid and 1.1 g of azobisisobutyronitrile (A.I.B.N.) are added under nitrogen to 65.4 g (0.4 equivalent as ethylene group). The mixture is then heated for 17 hours at 80° C.

After evaporation under reduced pressure, a viscous liquid product is obtained which is dark yellow in color and soluble in water at pH 6 in the presence of NaOH or triethanolamine.

EXAMPLE IX

Preparation of a mixture of compounds of formula (I) in which:
R denotes

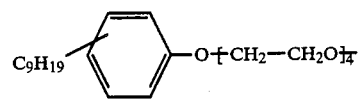

A denotes COONa
B denotes —OH
T denotes —O—
m=3 n=10 u=1 y=8 z=1

100 ml of ethanol, 20 g of ethyl thioundecanoate (0.079 mole) and 0.33 g of azobisisobutyronitrile (A.I.B.N.) are added under nitrogen to 13 g (0.079 equivalent as ethylene group) of compounds III prepared as in example VIII -1-.

The reaction mixture is heated under reflux for 24 hours. A clear, amber-colored solution is thus obtained.

8.7 g of an aqueous solution of sodium hydroxide containing 40% NaOH and 100 ml of water are added and the mixture is heated under reflux for 2 hours. After the solvents have been evaporated off under reduced pressure and the material acidified with hydrochloric acid, the organic phase is extracted in the presence of butanol. After removal of the butanol, 23.5 g of a pasty, brown-colored product are obtained, soluble in water in the presence of NaOH or of triethanolamine.

EXAMPLES OF APPLICATION

EXAMPLE 1

| Shampoo | |
|---|---|
| compounds of example VII | 0.5 g |
| non-ionic surfactant of formula R—CHOH—CH$_2$—O$\f$CH$_2$—CHOH—CH$_2$—O]$_n$H where R = mixture of C$_9$–C$_{12}$ alkyl radicals; n = 3.5 | 10 g |
| cationic polymer consisting of 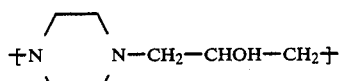 units prepared according to example 1 of U.S. Pat. No. 3,917,817 | 0.33 g |

| Shampoo | |
|---|---|
| water q.s. | 100 g |

This shampoo is in the form of a clear solution. Applied to dirty hair, it forms abundant foam; after rinsing, the wet hair disentangles easily. After drying, the hairstyle is characterised by good behavior.

EXAMPLE 2

| Rinse (rinsed lotion) | |
|---|---|
| compounds of example VI | 2 g |
| water q.s. | 100 g |
| pH adjusted to 9 | |

This lotion is applied to clean hair washed previously with the following shampoo:

| | |
|---|---|
| nonionic surfactant of formula<br>R—CHOH—CH$_2$O—(CH$_2$CHOH—CH$_2$—O)$_n$H<br>R = mixture of C$_9$-C$_{12}$ alkyl radicals; n = 3.5 | 10 g |
| cationic polymer consisting of<br>$+{}^\oplus$N(CH$_3$)(CH$_3$)—(CH$_2$)$_3$—${}^\oplus$N(CH$_3$)(CH$_3$)—(CH$_2$)$_6+$<br>Cl$^\ominus$ ... Cl$^\ominus$<br>units, prepared according to example 1 of U.S. Pat. No. 4,217,914 | 1.5 g |
| water q.s. | 100 g |

After application of the lotion to hair for several minutes, followed by a rinse, it is verified that the hair disentangles easily and that the hair-set behaves well.

EXAMPLE 3

Solutions of Hydrocortisone

Aqueous solutions containing approximately 10% by weight of compounds according to the invention and 0.6% of hydrocortisone are investigated after 15 days' storage at ambient temperature.

The decomposition of the hydrocortisone is followed by high performance liquid phase chromatography (HPLC).

The following table collates the results obtained, expressed as undecomposed hydrocortisone, for the compounds of examples I, II and III of the invention, compared to a conventional surfactant, potassium oleate.

| Compounds | Concentration by weight | pH | Undecomposed hydrocortisone, % |
|---|---|---|---|
| Example III | 8.6% | 9.5 | 100 |
| | | | 93.3 |
| Example I | 10.2% | 9.5 | 96.8 |
| Example II | 9.1% | 9.5 | 95.2 |
| K oleate* | 8.8% | 9.5 | 40 |

*Anionic surfactant, for comparison.

EXAMPLE 4

Dye Solution

The solubility of Orange OT identified in the Colour Index under No. 21,110 and the name "CI Pigment Orange 13" is investigated in aqueous solutions containing 0.3% by weight of compounds according to the invention.

8 μg of Orange OT are dispersed in 5 ml of aqueous solution containing 0.3% of active substance, by stirring by means of a shaker for 1 hour in an enclosure thermostated at 30° C. The material is then filtered on a 0.8 μ Millipore filter and the optical density of the filtrates is measured with a spectrophotometer at 495 nm.

| Compounds | Optical density |
|---|---|
| Example III | 0.805 |
| Example IV | 1.146 |
| Example IV/Example III (50/50 mixture) | 2.24 |
| K laurate | 0.023 |

Since the optical density is a function of the concentration of dye present in the solution, it can be seen that, relative to potassium laurate, the solubility of the dye in water in the presence of the compounds of the invention is increased by factors ranging from 35 to 100.

EXAMPLE 5

| Direct dyeing | |
|---|---|
| compounds of example V | 1 g |
| cetyl alcohol | 17 g |
| oleyl alcohol | 3 g |
| mixture of cetyl, stearyl and myristyl alcohols oxyethylenated with 13 moles of ethylene oxide | 6 g |
| 1-amino-2-nitro-4-(β-hydroxyethyl)aminobenzene | 0.3 g |
| 3-nitro-2-aminophenol | 0.12 g |
| 2-amino-2-methyl-1-propanol q.s. pH = 9 | |
| water q.s. | 100 g |

This cream is applied to chestnut hair for 20 minutes; after rinsing and washing, the hair has an auburn shade.

EXAMPLE 6

| Direct dyeing | |
|---|---|
| compounds of example III | 3 g |
| sodium alkyl (C$_{12}$-C$_{14}$) ether sulphate sold under the name SACTIPON 8533 by the company LEVER | 15 g |
| ethyl glycol | 8 g |
| 1-N-methylamino-2-nitro-4-N',N'-bis (β-hydroxyethyl)aminobenzene | 0.2 g |
| (4-nitro-3-methylamino)phenoxyethanol | 0.05 g |
| 2-N-β-hydroxyethylamino-5-nitroanisole | 0.05 g |
| 4-amino-3-nitrophenol | 0.1 g |
| citric acid q.s. pH = 8 | |
| water q.s. | 100 g |

This dyeing shampoo, applied to light chestnut hair, gives it, after rinsing, a coppery-golden shade.

EXAMPLE 7

| Oxidation dyeing | |
|---|---|
| compounds of example V | 2 g |
| non-ionic surfactant of formula:<br>R—O—(C$_2$H$_3$O(CH$_2$OH))$_2$H<br>R = oleyl | 5 g |
| non-ionic surfactant of formula:<br>R—O—(C$_2$H$_3$O(CH$_2$OH))$_4$H<br>R = oleyl | 5 g |

-continued

| Oxidation dyeing | |
|---|---|
| oleic acid | 5 g |
| oleylamine oxyethylenated with 12 moles of ethylene oxide, sold under the name ETHOMEEN 012 by the company ARMAK | 5 g |
| oleyl diethanolamide | 9 g |
| ethyl alcohol | 10 g |
| ethyl glycol | 12 g |
| p-phenylenediamine | 0.3 g |
| p-aminophenol | 0.4 g |
| resorcinol | 0.8 g |
| m-aminophenol | 0.4 g |
| hydroquinone | 0.15 g |
| ethylenediaminetetraacetic acid | 0.2 g |
| sodium bisulphite, 38° Be | 1.3 g |
| aqueous ammonia, 22° Be | 10 g |
| water q.s.p. | 100 g |

At the time of use, an equal weight of 20-volume hydrogen peroxide is added. Applied to light chestnut hair for 30 minutes, this liquid dye gives it, after rinsing, a natural golden blonde color.

EXAMPLE 8

| Direct dyeing | |
|---|---|
| compounds of example II | 0.5 g |
| compounds of example III | 0.5 g |
| compounds of example V | 2 g |
| nonylphenol oxyethylenated with 9 moles of ethylene oxide | 8 g |
| copra diethanolamide | 2 g |
| 2-butoxyethanol | 10 g |
| 1,4,5,8-tetraaminoanthraquinone | 0.05 g |
| diazoacetoquinone BSNZ Black sold by the company PCUK | 0.1 g |
| 2-methyl-4-amino-5-nitro-N-β-hydroxyethylaniline | 0.03 g |
| 4-N-β-hydroxyethylamino-2-nitro-N-hydroxyethylaniline | 0.2 g |
| water q.s. | 100 g |
| pH adjusted to 9.5 | |

Applied to dark chestnut hair for 30 minutes, this dye gives it, after rinsing, a purple-violet sheen.

EXAMPLE 9

| Direct dyeing | |
|---|---|
| compound of example VIII | 1 g |
| compound of example IX | 0.9 g |
| cetyl alcohol | 17 g |
| oleyl alcohol | 3 g |
| mixture of cetyl, stearyl and myristyl alcohols oxyethylenated with 13 moles of ethylene oxide | 6 g |
| 1-amino-2-nitro-4-(β-hydroxyethyl)aminobenzene | 0.2 g |
| 3-nitro-2-aminophenol | 0.12 g |
| 2-amino-2-methyl-1-propanol q.s. pH 9.5 | |
| water q.s. | 100 g |

This cream is applied to chestnut hair for 25 minutes; after rinsing and washing, the hair is of an auburn shade.

We claim:
1. Mixture of ionic polyethers of general formula:

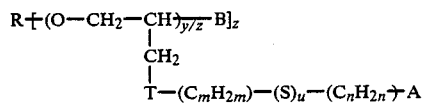

-continued in which:
R denotes an alkyl or alkenyl radical containing 1 to 20 carbon atoms, or an aryl or alkylaryl radical containing 6 to 20 carbon atoms, which are interrupted if appropriate by one or more oxygen atoms, R having the valency z, z being equal to 1 or 2;
y denotes an integer or decimal from 3 to 20;
T denotes an oxygen atom or a sulphur atom;
u denotes 0 or 1; when u=0, n=0; when u=1, n≠0 and R may be substituted by a radical S—$(C_nH_{2n})$—A;
m denotes an integer from 3 to 11;
n denotes either 0, or an integer from 1 to 11, the sum $m+n>0$
B denotes the OH group or the group A;
A being an ionic group chosen from the following groups:
(a) —COOM
(b) —$(CH_2)_{u'}$—(W)COOM, W denoting —$CH_2$—; —$CH_2$—$CH_2$—; or

u' being equal to 0 or 1 and u'=u
(c) —$CH_2$—O—$SO_3M$ in which M denotes an alkali metal, or an ammonium ion optionally substituted by one or more methyl, ethyl, hydroxyethyl, hydroxypropyl, methylhydroxypropyl, or methyldihydroxypropyl groups:

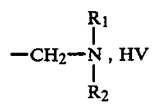 (d)

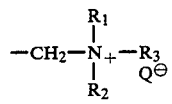 (e)

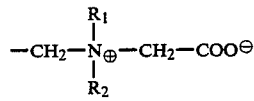 (f)

where $R_1$, $R_2$, $R_3$, which are identical or different, denote methyl, ethyl, hydroxyethyl or dihydroxypropyl radicals, $R_1$ and $R_2$ being also capable of forming with the nitrogen atom a heterocyclic amino or ammonio group; HV denotes an inorganic or organic acid;
Q⊖ denotes an anion;
(g)

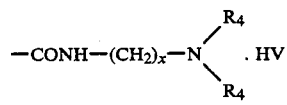 (g)

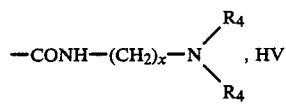  (g)

R$_4$ denoting methyl or ethyl, x=2 or 3 and HV having the same meaning as above (h)

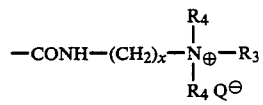  (h)

R$_3$ and Q having the same meaning as above (i)

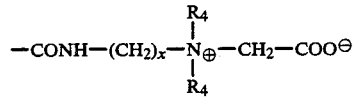  (i)

with the provision that when T=0 and u=0, A denotes only the group (b).

2. Mixture of ionic polyethers according to claim 1, characterised in that A denotes the groups (g), (h) or (i) and B denotes the OH group.

3. Mixture of ionic polyethers according to claim 1, characterised in that A denotes the groups (b), (c), (d), (e) or (f) and B denotes the group A.

4. Mixture of ionic polyethers according to claim 1, characterised in that A denotes the group (a) and B has either the meaning OH or the same meaning as A.

5. Mixture of ionic polyethers according to claim 1 characterised by the fact that $m=n\geqq 10$ and y denotes an integer or decimal from 5 to 20.

6. A cosmetic, pharmaceutical or textile processing composition comprising in an aqueous or aqueous-alcoholic vehicle from 0.1 to 35 percent by weight of a compound or mixture of compounds having the formula:

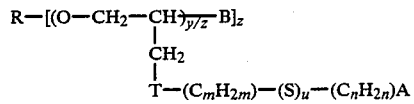  (I)

wherein

R represents alkyl or alkenyl containing 1–20 carbon atoms or aryl or alkyl aryl containing 6–20 carbon atoms, optionally interrupted by one or more oxygen atoms, R having the valency z wherein z is equal to 1 or 2, y represents an integer or decimal number ranging from 3 to 20, T represents an oxygen atom or a sulfur atom, u represents 0 or 1 with the proviso that when u=0, n=0 and when u=1, n≠0 and R can be substituted by a radical S—(C$_n$H$_{2n}$)—A, m represents an integer ranging from 3 to 11, n represents 0 or an integer ranging from 1 to 11, the sum of m+n>0, B represents OH or A, A represents an ionic group selected from the group consisting of (a) —COOM wherein M represents an alkali metal, or an ammonium ion optionally substitued by one or more of methyl, ethyl, hydroxyethyl, hydroxypropyl, methylhydroxypropyl or methyldihydroxypropyl, (b) —(CH$_2$)$_u$—S—(W)COOM, wherein W represents —CH$_2$—, —CH$_2$—CH$_2$— or

u' is equal to 0 or 1 and u'=u, (c) —CH$_2$—O—SO$_3$M, wherein M has the meaning given above,

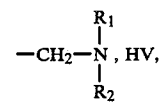  (d)

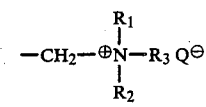  (e)

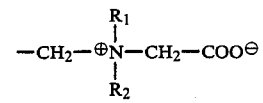  (f)

wherein

R$_1$, R$_2$ and R$_3$ each independently represent methyl, ethyl, hydroxyethyl or dihydroxypropyl, with R$_1$ and R$_2$ also being capable of forming with the nitrogen atom to which they are attached a heterocyclic amino or ammonio group, HV represents an inorganic or organic acid and Q$^\ominus$ represents an anion,

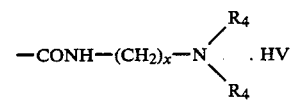  (g)

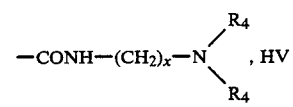  (g)

wherein R$_4$ represents methyl or ethyl, x=2 or 3 and HV has the meaning given above,

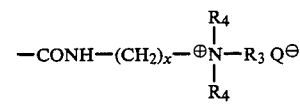  (h)

wherein R$_3$ and Q$^\ominus$ have the meanings given above, and

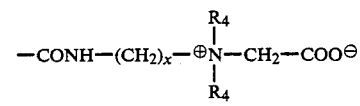  (i)

wherein R$_4$ has the meaning given above, with the proviso that when T represents an oxygen atom and u=0, A represents only definition (b) above.

7. The composition of claim 6 which also includes a C$_2$ to C$_4$ alcohol or Cellosolve.

8. The composition of claim 6 which also includes at least one of an anionic, cationic, amphoteric, zwitterionic or nonionic surface-active agent or polymer, a protein, colorant, pharmaceutically active principle, sunscreen, perfume, preserving agent, thickener, opacifier or electrolyte.

9. The composition of claim 6 which contains a mixture of said compounds of Formual (I), said mixture comprising at least one compound of Formula (I) wherein A contains an anionic group and at least one compound of Formula (I) wherein A contains a cationic group.

10. The composition of claim 6 which contains a mixture of (1) said compound or mixture of compounds having Formula (I) wherein A contains an anionic group and (2) a cationic polymer.

11. The composition of claim 6 which contains a mixture of (1) said compound or mixture of compounds having Formula (I) wherein A contains a cationic group and (2) an anionic polymer.

12. The composition of claim 6 which also contains an effective amount of a dye or dye precursor.

13. The composition of claim 6 which also contains an effective amount of a pharmaceutically active compound.

14. The composition of claim 13 wherein said pharmaceutically active compound is hydrocortisone.

15. The composition of claim 6 which also includes an effective amount of a textile dye.

16. A mixture of ionic polyethers of the formula

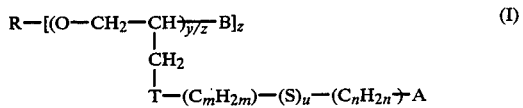
(I)

wherein
R represents alkyl or alkenyl containing 1-20 carbon atoms, or aryl or alkyl aryl containing 6-20 carbon atoms, optionally interrupted by one or more oxygen atoms, R having the valency z wherein z is equal to 1 or 2,
y represents an integer or decimal number ranging from 3 to 20,
T represents an oxygen atom or a sulfur atom,
u represents 0 or 1 with the proviso that when u=0, n =0 and when u=1, n≠0 and R can be substituted by S—(C$_n$H$_{2n}$)—A,
m represents an integer ranging from 3 to 11,
n represents 0 or an integer ranging from 1 to 11, the sum of m+n>0,
B represents —OH and
A represents —COOM wherein M represents alkali metal or an ammonium ion optionally substituted by one or more of methyl, ethyl, hydroxyethyl, hydroxypropyl, methylhydroxypropyl or methyldihydroxypropyl,
with the proviso that T is not an oxygen atom when u=0.

17. A mixture consisting of ionic polyethers of the formula

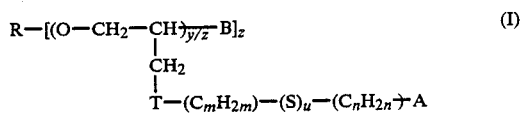
(I)

wherein
R represents Na—OCO—CH$_2$—S—C$_{11}$H$_{22}$—,
A represents —COONa
B represents —OH,
T represents an oxygen atom,
m=11, n=1, u=1, y=5 and z=1.

18. A mixture consisting of ionic polyethers of the formula

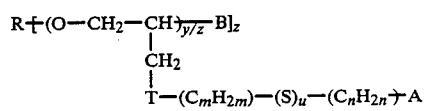

wherein
R represents Na—OCO—CH$_2$S—C$_{11}$H$_{22}$, —
A represents —COO—Na,
B represents —OH,
T represents an oxygen atom,
m=11, n=1, u=1, y=10 and 19. A mixture consisting of ionic polyethers of the formula

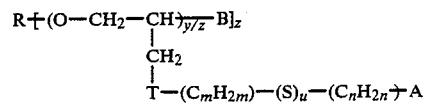

wherein
R represents C$_{12}$H$_{25}$,
A represents —COONa,
B represents —OH,
T represents a sulfur atom, m=11, n=0, u=0, y=10 and z=1.

20. A mixture consisting of ionic polyethers of the formula

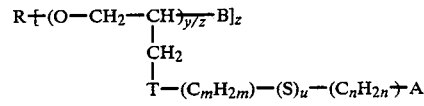

wherein
R represents C$_{12}$H$_{25}$
A=B=

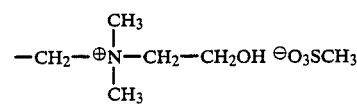

T represents a sulfur atom,
m=11, n=0, u=0, y=10 and z=1.

21. A mixture consisting of ionic polyethers of the formula

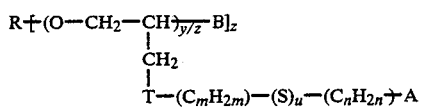

wherein

R represents $C_{12}H_{25}$,

A represents —COONa,

B represents —OH,

T represents an oxygen atom, $m=3$, $n=10$, $u=1$, $y=10$ and $z=1$.

22. A mixture consisting of ionic polyethers of the formula

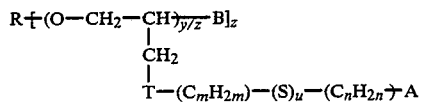

wherein

R represents $C_{12}H_{25}$,

A represents —COONa,

B represents —OH,

T represents an oxygen atom, $m=3$, $n=1$, $u=1$, $y=10$ and $z=1$.

23. An ionic polyether of the formula

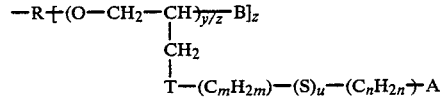

wherein

R represents

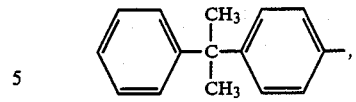

A represents —COONa,

B represents —OH,

T represents an oxygen atom, $m=3$, $n=1$, $u=1$, $y=15$ and $z=2$.

24. A mixture consisting of ionic polyethers of the formula

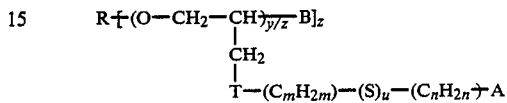

wherein

R represents

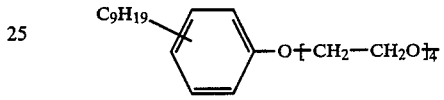

A represents —S—$CH_2$—$CH_2$—COOH,

B represents —OH

T represents an oxygen atom, $m=3$, $n=0$, $u=0$, $y=8$ and $z=1$.

25. A mixture consisting of ionic polyethers of the formula

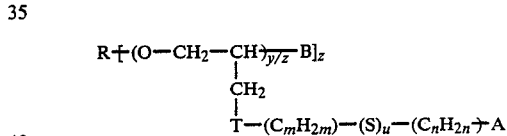

wherein

R represents

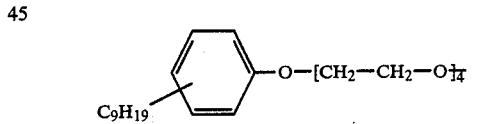

A represents —COONa,

B represents —OH,

T represents an oxygen atom, $m=3$, $n=10$, $u=1$, $y=8$ and $z=1$.

* * * * *